United States Patent [19]

Kawaguchi et al.

[11] Patent Number: 5,658,466
[45] Date of Patent: Aug. 19, 1997

[54] METHOD OF STERILIZING A BLOOD DIALYZER HAVING SEMIPERMEABLE POLYMERIC MEMBRANES BY γ-RAY IRRADIATION

[75] Inventors: Takeyuki Kawaguchi, Iwakuni; Hironori Matsuda, Hino; Masaaki Tsukioka; Takahiro Daido, both of Iwakuni, all of Japan

[73] Assignee: Teijin Limited, Osaka, Japan

[21] Appl. No.: 404,311

[22] Filed: Mar. 15, 1995

[30] Foreign Application Priority Data

| Mar. 16, 1994 | [JP] | Japan | 6-045568 |
| Mar. 16, 1994 | [JP] | Japan | 6-045569 |
| Apr. 26, 1994 | [JP] | Japan | 6-088553 |
| Dec. 5, 1994 | [JP] | Japan | 6-300752 |

[51] Int. Cl.$^6$ .............. A61L 2/00; A61L 2/08; B01D 65/02
[52] U.S. Cl. .............. 210/748; 210/321.69; 210/764; 422/1; 422/22; 422/23
[58] Field of Search .......... 210/321.69, 500.21, 210/748, 764, 500.23; 422/1, 22, 23, 24, 28, 44, 26

[56] References Cited

U.S. PATENT DOCUMENTS

| 4,148,606 | 4/1979 | Morita et al. | 422/21 |
| 4,377,010 | 3/1983 | Fydelor et al. | 210/500.38 |
| 4,543,221 | 9/1985 | Chen et al. | 210/500.23 |
| 4,609,728 | 9/1986 | Spranger et al. | 422/26 |
| 4,673,506 | 6/1987 | Henne et al. | 210/636 |
| 4,767,538 | 8/1988 | Jakubowski et al. | 210/636 |
| 4,813,210 | 3/1989 | Masuda et al. | 53/425 |
| 5,340,480 | 8/1994 | Kawata et al. | 210/500.23 |

FOREIGN PATENT DOCUMENTS

| 0131143 | 1/1985 | European Pat. Off. . |
| 0218003 | 4/1987 | European Pat. Off. . |
| 0359366 | 3/1990 | European Pat. Off. . |
| 2365348 | 4/1978 | France . |
| 3319504 | 11/1984 | Germany . |
| 3439572 | 6/1985 | Germany . |
| 52-99697 | 8/1977 | Japan . |
| 59-192373 | 10/1984 | Japan . |
| 2088074 | 4/1990 | Japan . |
| 5192397 | 8/1993 | Japan . |

OTHER PUBLICATIONS

Database WPI, Derwent Publ., Abstract of Japanese Appln. No. 90-142942, JP-A-02 988 074, Mar. 28, 1990.
Database WPI, Derwent Publ., Abstract of Japanese Appln. No. 93-277527, JP-A-05 192 397, Aug. 3, 1993.
Database WPI, Derwent Publ., Abstract of Japanese Appln. No. 92-091525, JP-A-04 033 657, Feb. 5, 1992.

*Primary Examiner*—John Kim
*Attorney, Agent, or Firm*—Burgess, Ryan & Wayne

[57] ABSTRACT

A blood dialyzer having semipermeable polymeric dialyzing membranes is sterilized by impregnating the dialyzing membranes, for example, dialyzing hollow fibers, with an aqueous solution of a γ-ray-absorbent and water-soluble dihydric aliphatic alcohol and irradiating γ-rays to the dialyzing membranes, to prevent the deterioration of the dialyzing membranes and the generation of ultraviolet-ray-absorbent substance in the dialyzing membrane.

17 Claims, No Drawings

METHOD OF STERILIZING A BLOOD DIALYZER HAVING SEMIPERMEABLE POLYMERIC MEMBRANES BY γ-RAY IRRADIATION

BACKGROUND OF THE INVENTION

1. Field of the Invention

The present invention relates to a method of sterilizing a blood dialyzer having semipermeable membranes by γ-ray irradiation. More particularly, the present invention relates to a method of sterilizing a blood dialyzer having semipermeable polymeric membranes by irradiating the dialyzer with γ-rays, without deterioration of the polymeric membranes, while preventing an increase in the ultraviolet ray-absorbing property of the polymeric membranes due to the γ-ray irradiation.

2. Description of the Related Art

As a typical method of sterilizing medical devices, for example, blood dialyzer having semipermeable polymeric membranes, an ethylene oxide gas sterilizing method, a high pressure steam sterilizing method and a γ-ray sterilizing method are known. These sterilizing methods have both merits and demerits. In recent years, the high pressure steam sterilizing method and the γ-ray sterilizing method have been commonly utilized due the merits of less residual toxicity and extreme ease of operation.

Nevertheless, the utilization of the high pressure steam sterilizing method is restricted to semipermeable membranes having a high heat resistance. Also, it is known that the γ-ray sterilizing method is not appropriate for membrane materials comprising cellulose, cellulose esters or polymethyl methacrylate which have poor resistance to γ-rays. Therefore, it was believed that the γ-ray sterilizing method was difficult to be practically utilized to sterilize the blood dialyzer having semipermeable membranes made from the above-mentioned polymeric materials.

A specific method of sterilizing a blood dialyzer having semipermeable membranes made from a polymer having a low γ-ray resistance by γ-ray irradiation is disclosed in Japanese Unexamined Patent Publication (Kokai) No. 59-192,373. In this specific method, the γ-ray irradiation is carried out in an inert gas atmosphere comprising carbon dioxide or nitrogen gas. This Japanese publication discloses that when the γ-ray irradiation is applied to the membranes in an γ-ray active (absorbent) gas atmosphere, for example, an oxygen gas atmosphere, the membranes are oxidized and thus deteriorate. This Japanese publication further states that by the specific method thereof, the membranes can be sterilized by the γ-ray irradiation in a dry condition, while preventing the deterioration of the membranes.

This method is, however, disadvantageous in that since the resultant sterilized blood dialyzer is in a dry condition, the semipermeable membranes must be wetted and bubbles formed in the blood dialyzer must be completely removed before the blood dialyzer is subjected to practical use, and these operations require much labor and time and thus the omission of these operations is strongly demanded by medical institutions.

Also, Japanese Unexamined Patent Publication (Kokai) No. 52-99,679 discloses a method by which blood dialyzing membranes can be sterilized in a wetted condition by γ-ray irradiation. In accordance with this method, the γ-ray sterilizing method can be applied to the blood dialyzing membranes comprising cellulose or polymethyl methacrylate in a water-wetted condition.

The inventors of the present invention have investigated this method and found that when the γ-ray sterilization is applied to a semipermeable polymeric membrane wetted only with water in a saturation amount or more, it is difficult to fully sterilize the polymeric membranes without substantial deterioration thereof. Especially, it has been confirmed that when this method is applied to semipermeable cellulose ester membranes, the above-mentioned difficulty significantly increases.

Further, Japanese Unexamined Patent Publication (Kokai) No. 5-192,397 discloses that when a blood dialyzer having semipermeable polymeric dialyzing membranes is sterilized by a γ-ray irradiation, the derioration of the polymeric dialyzing membranes can be prevented by packing the blood dialyzer with an aqueous solution of 0.1 to 5.0% by weight of glycerol. This method is advantageous in that the deterioration of the dialyzing membranes can be avoided. However, this method is disadvantageous in that the γ-ray irradiation causes the γ-ray-irradiated aqueous glycerol solution packed in the blood dialyzer to contain a γ-ray reaction product which exhibits an undesirable ultraviolet ray-absorbing property, and sometimes, an extract dissolved out from the sterilized polymeric membranes into the aqueous glycerol solution exhibits an ultraviolet ray-absorption value exceeding 0.1 which is an upper limit of safety margin of the extract.

Also, the aqueous glycerol solution allows bacteria to proliferate before the γ-ray sterilization. Therefore, after the γ-ray irradiation, the sterilized aqueous glycerol solution includes an increased amount of dead bacteria.

Accordingly, there has been a strong demand for a new γ-ray sterilizing method for a blood dialyzer having semipermeable polymeric dialyzing membranes which can prevent or restrict the generation of an γ-ray reaction product having an ultraviolet ray-absorption value exceeding the margin of safety of the blood dialyzer.

SUMMARY OF THE INVENTION

An object of the present invention is to provide a method of sterilizing a blood dialyzer having semipermeable polymeric dialyzing membranes by γ-ray irradiation with a high sterilization efficiency, without derioration of the dialyzing membranes even where the γ-ray irradiation is applied to the dialyzing membranes in a wetted condition.

Another object of the present invention is to provide a method of sterilizing a blood dialyzer having semipermeable polymeric dialyzing membranes by γ-ray irradiation with a high sterilization efficiency, without causing or while restricting a generation of an γ-ray reaction product having an ultraviolet ray-absorption value exceeding the margin of safety.

The above-mentioned objects can be attained by the method of the present invention for sterilizing a blood dialyzer having semipermeable polymeric dialyzing membranes by γ-ray irradiation, comprising the steps of:

impregnating semipermeable polymeric dialyzing membranes in a blood dialyzer with an aqueous solution of at least one γ-ray-absorbent and a water-soluble dihydric aliphatic alcohol; and irradiating γ-rays to the semipermeable polymeric dialyzing membranes impregnated with the aqueous solution of the dihydric aliphatic alcohol.

DESCRIPTION OF THE PREFERRED EMBODIMENT

The sterilizing method of the present invention by γ-ray irradiation is applied to a blood dialyzer having semipermeable polymeric dialyzing membranes preferably contained in a cylindrical case (container).

In the first step of the method of the present invention, the semipermeable polymeric dialyzing membranes in the blood dialyzer are impregnated with an aqueous solution of at least one γ-ray-absorbent and a water-soluble dihydric aliphatic alcohol.

The aqueous solution of the dihydric aliphatic alcohol effectively protects the dialyzing membranes from deterioration thereof and prevents the generation of an γ-ray reaction product having an enhanced ultraviolet-ray absorption.

The protection mechanism derived from the aqueous solution of the dihydric aliphatic alcohol is not completely clear. It is assumed, however, that when the γ-rays are irradiated, the dialyzing membrane polymer releases electrons and generates cationic radicals, and the cationic radicals are chemically stabilized by reacting with hydrogen withdrawn from the divalent aliphatic alcohol, so as to stop or restrict the deteriorative chain reaction of the dialyzing membrane polymer.

The polymers for forming the semipermeable polymeric dialyzing membranes are not limited to a specific type of polymers, as long as they have a sufficient blood dialyzing property. Preferably the dialyzing membranes comprise at least one polymeric material selected from the group consisting of cellulose, cellulose esters, for example, cellulose diacetate and cellulose triacetate, alkyl methacrylate homopolymers and copolymers in which the alkyl group preferably has 1 to 4 carbon atoms, for example, polymethyl methacrylate, polyethyl methacrylate, methyl methacrylate-methacryl sulfonate copolymers and methyl methacrylate-butyl acrylate copolymers, polyvinyl alcohol, partially saponified polyvinyl acetates, polysulfone, acrylonitrile homopolymer and copolymers, for example, polyacrylonitrile, acrylonitrile-methacryl sulfonate copolymers and acrylonitrile-acrylic acid copolymers, polyethylene and polyamides. Among the above-mentioned polymers, the cellulose esters, for example, cellulose diacetate and cellulose triacetate are advantageously employed for the formation of the dialyzing membranes.

There is no specific limitation to the form of the dialyzing membranes as long as they can effectively dialyze the blood. Preferably, the dialyzing membranes usable for the present invention are in the form of hollow fibers. Particularly, a regenerated cellulose or a cellulose ester, more preferably cellulose diacetate or cellulose triacetate, are utilized for the blood dialyzing hollow fibers of the present invention.

The dihydric aliphatic alcohol usable for the method of the present invention is γ-ray absorbent and water-soluble and preferably selected from the group consisting of the compounds of the formulae (I) and (II):

and

wherein n represents an integer of 2 to 5, $m_1$ represents an integer of 1 to 50, and $m_2$ represents an integer of 1 to 10.

Preferably, the dihydric aliphatic alcohol usable for the method of the present invention is selected from the group consisting of ethylene glycol, propylene glycol, polypropylene glycol, polyethylene glycol, ethylene glycol-propylene glycol copolymers. These dihydric aliphatic alcohols are used alone or in a mixture of two or more thereof. Among the above-mentioned compounds, propylene glycol, polypropylene glycol and mixtures thereof are more preferably used and propylene glycol is still more preferably employed for the method of the present invention.

The dihydric aliphatic alcohols usable for the present invention are not limited to a specific group thereof as long as they are water-soluble and γ-ray absorbent. Generally, the dihydric aliphatic alcohols preferably have a molecular weight of 1500 or less, more preferably 1000 or less.

In the method of the present invention, the dihydric aliphatic alcohol is present preferably in a concentration of 0.1 to 80% by weight, more preferably 0.2 to 50% by weight, still more preferably 0.2 to 20% by weight, further preferably 0.5 to 10% by weight, in the aqueous solution. Also, the dihydric aliphatic alcohol is present preferably in an amount of 3 to 300%, more preferably 10 to 200%, based on the total weight of the semipermeable polymeric dialyzing membranes.

The concentration of the dihydric aliphatic alcohol in the aqueous solution thereof is variable depending on the manner in which the aqueous solution of the dihydric aliphatic alcohol is applied to the dialyzer.

For example, where the aqueous dihydric aliphatic alcohol solution is impregnated only in the dialyzing membranes, the concentration of the dihydric aliphatic alcohol is preferably in the range of from 500 to 1000 g/l. In this use, the dihydric aliphatic alcohol is present in the above-mentioned relatively high concentration and in an amount of 200 to 300% based on the total dry weight of the dialyzing membranes.

This high concentration of the aqueous dihydric aliphatic alcohol solution impregnated in the dialyzing membranes serves as a humectant for the dialyzing membranes after the sterilizing step is completed.

Where the aqueous dihydric aliphatic alcohol solution is packed in the blood dialyzer so that the dialyzing membranes are immersed in and impregnated with the aqueous solution, the concentration of the dihydric aliphatic alcohol in the aqueous solution is preferably in the range of from 5 to 50 g/l. In this case, the dihydric aliphatic alcohol is present in a relatively low concentration and in an amount of 15 to 150% based on the total weight of the dialyzing membranes.

The aqueous solution of the dihydric aliphatic alcohol can be prepared by dissolving the dihydric aliphatic alcohol and optionally a pH-adjuster in water purified by an ultrafiltration or a reverse osmosis filtration. The aqueous solution of the dihydric aliphatic alcohol may further contain a water-conservative agent, for example, formaldehyde, if necessary.

In the preparation of the aqueous solution of the dihydric aliphatic alcohol, the pH of the aqueous solution is preferably adjusted to a level of 4 to 7, before the γ-ray irradiation.

If the pH of the aqueous solution of the dihydric aliphatic alcohol is lower than 4.0 or higher than 7.0, the dialyzing membranes are sometimes decomposed or deteriorated. For example, where the dialyzing membranes comprise a cellulose ester, the pH lower than 4.0 or higher than 7.0 sometimes causes a risk of undesirable hydrolysis of the side chains and/or the backbone chains of the cellulose ester molecules.

The inventors of the present invention have confirmed that when the pH of the aqueous solution of the dihydric aliphatic alcohol in the dialyzer is changed to a level of 3.8 or 7.8 by the γ-ray irradiation, the polymeric dialyzing membranes are significantly deteriorated and the sieving coefficient of the membranes with respect to dextran having a molecular weight of 70,000, is significantly increased.

In the second step of the method of the present invention, γ-rays are irradiated toward the dialyzing membrane impregnated with the aqueous solution of the dihydric aliphatic alcohol.

In the method of the present invention, preferably, during the entire period of and after the γ-ray irradiation, the pH of the aqueous solution of the dihydric aliphatic alcohol is maintained at a level of 4 to 7, more preferably 5 to 7. The reduction in the pH of the aqueous dihydric aliphatic alcohol solution is derived from a decomposition or deterioration of the dialyzing membranes. Also, the reduced pH promotes the decomposition or deterioration of the dialyzing membranes during and after the γ-ray irradiation.

For the purpose of controlling the pH of the aqueous dihydric aliphatic alcohol to a level of 4 to 7 during the entire period of and after the γ-ray irradiation, a pH-adjuster is preferably added to the aqueous solution.

The pH-adjuster preferably comprises at least one member selected from the group consisting of phosphate buffer solutions and borate buffer solutions.

In the method of the present invention, it is preferred that a difference in pH of the aqueous solution of the dihydric aliphatic alcohol between before and after the γ-ray irradiation be in the range of less than 1.5, more preferably 1.0 or less, in view of the safety margin of the aqueous solution contained in the blood dialyzer for the application thereof to a living human body. Where the dialyzing membranes comprise a cellulose ester, the pH control of the aqueous solution of the dihydric aliphatic alcohol is preferably effected by addition of a phosphate buffer solution.

The γ-ray sterilizing procedure can be effected by packing the dialyzer with the aqueous solution of the dihydric aliphatic alcohol or impregnating the dialyzing membranes in the dialyzer with the aqueous solution, optionally sealing the dialyzer, and applying a γ-ray irradiation to the dialyzer. Alternatively, the above-mentioned dialyzer can be placed in a sterilizing bag and the γ-ray irradiation can be applied to the dialyzer through the bag.

The γ-ray irradiation is can be carried out under the usual conditions.

The absorbed dose of the γ-rays is preferably in the range of from 10 to 50 kGy. For example, the absorbed dose of the γ-rays for a cellulose ester hollow fibers is preferably 20 to 50 kGy.

If necessary, the blood dialyzer may be pre-sterilized by a heat treatment, for example, at a temperature of 40° to 70° C. for a time of 10 to 60 minutes, so as to stabilize the performance of the dialyzer before the γ-ray sterilization.

Preferably, during the γ-ray irradiation, the temperature of the semipermeable polymeric dialyzing membranes impregnated with the aqueous solution of the dihydric aliphatic alcohol is maintained at a level of 50° C. or less. If the temperature is higher than 50° C., an undesirable deterioration of the dialyzing membrane may be promoted.

In an embodiment of the method of the present invention, the aqueous solution of the dihydric aliphatic alcohol is saturated with oxygen dissolved therein. The oxygen-saturated aqueous solution of the dihydric aliphatic alcohol optionally contains a pH-adjuster and/or a water-conservative agent. Also, the temperature of the dialyzing membranes impregnated with the aqueous solution of the dihydric aliphatic alcohol is preferably maintained at a level of 50° C. or less. If the temperature is higher than 50° C., the dissolved oxygen is liberated from the aqueous solution and deteriorate the dialyzing membrane.

The oxygen-saturated aqueous solution of the dihydric aliphatic alcohol effectively protects the dialyzing membranes from deterioration.

Before the present invention, it was believed that oxygen dissolved in the aqueous solution of the dihydric aliphatic alcohol promotes the deterioration of the dialyzing membranes and thus the γ-ray irradiation should be applied in the absence of oxygen. However, in the case where the aqueous solution of the aqueous solution of the specific dihydric aliphatic alcohol is employed to prevent the deterioration of the dialyzing membranes, the oxygen saturation surprisingly promotes the protection effect of the aqueous solution of the dihydric aliphatic alcohol on the dialyzing membranes.

The protection mechanism by the dissolved oxygen is not completely clarified. It is assumed that the γ-rays irradiated to the aqueous solution of the dihydric aliphatic alcohol and the dialyzing membranes activate the dissolved oxygen in the aqueous solution so as to generate ozone, without deteriorating the dialyzing membranes. The ozone sterilizes the dialyzing membranes and simultaneously protects the dialyzing membranes from deterioration thereof. It is assumed that when the γ-rays are irradiated, the polymeric material of the dialyzing membranes generate reactive cationic radicals, and the cationic radicals are stabilized by a hydrogen-withdrawing reaction from the dihydric aliphatic alcohol, so as to prevent or restrict the deteriorative chain reaction of the dialyzing membrane polymer. On the other hand, electrons released from the dialyzing membrane polymer are quenched by the dissolved oxygen in the aqueous solution. The above-mentioned reactions synergistically serve to effectively prevent the decomposition or deterioration of the dialyzing membranes due to the γ-ray irradiation.

In an example of the preparation of the oxygen-saturated aqueous solution of the dihydric aliphatic alcohol, first, water is saturated with oxygen, and second, the dihydric aliphatic alcohol is dissolved in the oxygen-saturated water. In another example, the dihydric aliphatic alcohol is dissolved in water, and then the resultant aqueous solution is saturated by oxygen by blowing oxygen gas or air into the aqueous solution.

The blood dialyzer to which the sterilizing method of the present invention can be applied, is prepared, for example, as follows.

A plurality of core-in-sheath type composite fibers each comprising a core portion consisting of a water-insoluble core liquid, for example, a liquid paraffin, and a sheath portion consisting of a fiber forming polymer, for example, cellulose triacetate and surrounding the core portion, are subjected to a removal of almost all of the core liquid from the core portion, to convert the core-in-sheath type composite fibers to hollow fibers. The hollow fibers are bundled to form a cylindrical case having open ends thereof to form a blood dialyzer module, and the end portions of spaces left between the hollow fiber peripheries and between the hollow fiber bundle and the inside surface of the cylindrical case, are sealed with a bonding resin material, and the bundle is fixed to the cylindrical case at the end portions thereof. Then, the hollow fibers are cleaned with a cleaning liquid, for example, a lower aliphatic monohydric alcohol or an aqueous solution of a surfactant, to remove the residual core liquid and solvent from the hollow fibers.

Where a blood dialyzer module having a plurality of dialyzing hollow fibers and packed with water or an aqueous solution of, for example, propylene glycol or ethylene glycol, is supplied to a blood dialyzing practice, (a) the water or aqueous solution is withdrawn in a physical manner from the blood dialyzer module under such a condition that the dialyzing hollow fibers are maintained in a wetted state, (b) an aqueous solution of a humectant is flowed through the hollow spaces of the hollow fibers in such a manner that the aqueous humectant solution is not allowed to flow out to the outside of the hollow fibers through the outer surfaces of the hollow fibers and the hollow fibers are impregnated with the aqueous humectant solution, and then (c) a portion of the aqueous humectant solution remaining in the hollow spaces of the hollow fibers is removed in a physical manner from the hollow fibers under such a condition that the hollow fibers are maintained in a semi-wetted condition.

The thus prepared blood dialyzer is subjected to the γ-ray sterilizing method of the present invention.

In the water or aqueous solution-withdrawing physical step (a), the resultant hollow fibers maintained in a wetted condition preferably contain water or the aqueous solution in an amount of 10 to 500% by weight, more preferably 100 to 300% by weight, based on the total dry weight of the hollow fibers. The physical withdrawal of the water or aqueous solution can be effected by allowing the water or aqueous solution to gravitationally fall down, pushing out the water or aqueous solution by compressed air, or centrifugally removing the water or aqueous solution from the hollow fibers. This withdrawal operation (a) is carried out preferably at a temperature of from room temperature to 70° C., more preferably from room temperature to 50° C.

In the humectant-impregnating step (b), the humectant is preferably selected from dihydric aliphatic alcohols, for example, ethylene glycol, propylene glycol, and water-soluble polyethylene glycol and polypropylene glycol, and contained in a content of 30 to 90% by weight, more preferably 50 to 80% by weight in the aqueous solution thereof.

In this step (b), the aqueous humectant solution is impregnated in the hollow fibers preferably in such a manner that the solution-feed side of the hollow fibers are maintained under a positive pressure or a light negative pressure compared with the pressure in the solution-delivery side of the hollow fibers, for example, the pressure in the solution-feed side of the hollow fibers is controlled to a level of, preferably about −500 to +2,000 mmHg, more preferably +10 to 760 mmHg.

Where the hollow fibers comprise cellulose triacetate, the solution-feed side pressure of the hollow fibers is controlled to a level of 50 to 560 mmHg. The solution-delivery side pressure of the hollow fibers may be lightly negative.

Preferably, the humectant-impregnating step is carried out at a temperature of 0° C. to 70° C. for 30 seconds to 20 minutes, more preferably from room temperature to 50° C. for one to 10 minutes.

The aqueous humectant solution-removing step (c) can be effected by the same procedures as in the water or aqueous solution-withdrawal step (a), while keeping the hollow fibers at a semi-wetted state. Optionally, after the aqueous humectant solution-removing step (c), a pressure is applied to the solution-feed side of the hollow fibers and then this pressure is released instantaneously so as to remove an excessive amount of the aqueous humectant solution from the hollow spaces and the hollow fiber bodies.

If necessary, the semi-wetted dialyzing hollow fibers are further dried by blowing air, heating (using hot air, a heater or high frequency waves), or steam drying (including solvent vapor-drying). Preferably, the drying is effected by blowing air at room temperature from the blood-feed or delivery side to the blood-delivery or feed side of the hollow fibers.

The above-mentioned semi-wetted hollow fibers are advantageous in that they have no risk of freezing even at a low temperature, the resultant blood dialyzer module has a light weight and a high dimensional stability and thus can be easily stored and transported.

EXAMPLES

The present invention will be further explained by the following examples which are merely representative and do not intend to restrict the scope of the present invention in any way.

In the examples, the following tests were applied to the resultant dialyzing hollow fibers.

(1) Dextran 70,000 sieving coefficient (Dextran 70,000 SC) An aqueous solution of 0.01% by weight of dextran with a molecular weight of 70,000 was subjected to a permeation through hollow fiber bodies under a pressure of 10 mmHg (1,332.2 Pa). The concentration of dextran in the resultant permeated solution was measured. The dextran 70,000 SC was calculated from the measured data.

(2) Pressure resistance

Air pressure was applied to the blood-delivery side of the dialyzing hollow fibers, and a level of the applied air pressure at which air bubbles were found in the blood-feed side of the hollow fibers was measured. The pressure resistance of the hollow fibers was represented by the measured air-bubble-forming pressure.

(3) Ultraviolet-ray-absorption

The ultraviolet-ray-absorption of the hollow fibers before or after the γ-ray sterilization was determined by the following procedures.

The hollow fibers to be tested were dried at a temperature of 80° C. for 4 hours. A sample in a weight of 1.5 g of the dried hollow fibers was immersed in 150 ml of distilled water and heated at a temperature of 70° C. for one hour to extract the hollow fibers. The resultant extract was subjected to an ultraviolet-ray-absorption measurement at a wavelength of from 220 nm to 300 nm by using a spectrophotometer. The ultraviolet-ray-absorption value of the extract of the hollow fibers was represented by a peak value of the measured absorption.

Example 1

In Example 1, an aqueous solution was prepared by dissolving 5% by weight of a polypropylene glycol having a molecular weight of 400 in water purified by a reverse osmosis filtration.

A blood dialyzer module having a bundle consisting of 480 individual cellulose triacetate hollow fibers each having a length of about 300 mm, an outside diameter of 230 μm, an inside diameter of 200 μm and a membrane thickness of 15 μm, and packed in a cylindrical case made from a clear polycarbonate resin and having a length of about 300 mm and an inside diameter of 35 mm, was filled by the above-mentioned aqueous polypropylene glycol solution so as to impregnate the hollow fibers with the aqueous polypropylene glycol solution, and sealed.

Then, the blood dialyzer module was subjected to a γ-ray irradiation at a temperature of room temperature ±10° C. at an absorbed dose of 25 kGy for 20 hours, to sterilize the hollow fibers.

The test results are shown in Table 1.

Examples 2 and 3 and Comparative Examples 1 to 3

In each of Examples 2 and 3 and Comparative Examples 1 to 3, the same procedures as in Example 1 were carried out with the following exceptions.

In Example 2, the 5% by weight of polypropylene glycol was replaced by a mixture of 5% by weight of propylene glycol and 0.2% by weight of a phosphate buffer solution.

In Example 3, the 5% by weight of polypropylene glycol was replaced by a mixture of 5% by weight of the same polypropylene glycol as in Example 1 and 0.2% by weight of the phosphate buffer solution.

In Comparative Example 1, the polypropylene glycol was omitted, namely the blood dialyzer module was filled by the water purified by the reverse osmosis filtration.

In Comparative Example 2, the polypropylene glycol was replaced by 5% by weight of glycerol.

In Comparative Example 3, the polypropylene glycol was replaced by 0.2% by weight of the same phosphate buffer solution as in Example 2.

The test results are shown in Table 1.

In Comparative Examples 1 and 3, the absence of the dihydric aliphatic alcohol caused the dextran 70,000 sieve coefficient to significantly increase.

In Comparative Example 2 in which glycerol was employed in place of the dihydric aliphatic alcohol, while the change in the dextran 70,000 sieve coefficient due to the γ-ray irradiation was very small, the change in the ultraviolet-ray-absorption of the hollow fiber extract due to the γ-ray irradiation was 0.115 (0.150–0.035) which exceeded the upper limit of the margin of safety of the extract. Accordingly, it was confirmed that surprisingly, the effect of the dihydric aliphatic alcohol on the protection of the hollow fibers from the deterioration and decomposition thereof due to the γ-ray irradiation, is significantly higher than that of glycerol.

TABLE 1

| | | Item | | | | | |
|---|---|---|---|---|---|---|---|
| | | Before γ-ray irradiation | | | After γ-ray irradiation | | |
| Example No. | Additive (content, wt %) | Dextran 70,000 SC | pH | UV-absorption of hollow fibers | Dextran 70,000 SC | pH | UV-absorption of hollow fibers |
| Example 1 | Polypropylene glycol (5 wt %) | 0.067 | 6.0 | 0.030 | 0.065 | 3.9 | 0.032 |
| Example 2 | Propylene glycol (5 wt %) & Phosphate buffer solution (0.2 wt %) | 0.065 | 6.7 | 0.032 | 0.065 | 6.3 | 0.035 |
| Example 3 | Polypropylene glycol (5 wt %) & Phosphate buffer solution (0.2 wt %) | 0.068 | 6.8 | — | 0.066 | 6.5 | — |
| Comparative Example 1 | None | 0.068 | 6.8 | — | 0.089 | 3.3 | — |
| Comparative Example 2 | Glycerol (5 wt %) | 0.066 | 6.7 | 0.035 | 0.069 | 3.8 | 0.150 |
| Comparative Example 3 | Phosphate buffer solution (0.2 wt %) | 0.071 | 6.8 | — | 0.089 | 6.5 | — |

Table 1 clearly shows that in Examples 1 to 3 in accordance with the present invention, the Dextran 70,000 sieve coefficient of the hollow fibers after the γ-ray irradiation is substantially the same as that before the γ-ray irradiation. Also, in Examples 1 and 2, a difference in the ultraviolet-ray-absorption of the hollow fiber extract between before and after the γ-ray irradiation is significantly less than 0.1 which is an upper limit of safety margin of the blood dialyzing membrances. These test results indicate that the specific aqueous solution of the dihydric aliphatic alcohol and optionally a phosphate buffer solution effectively protect the hollow fibers from deterioration and decomposition thereof due to the γ-ray irradiation. Also, the phosphate buffer solution effectively prevents or restricts a change in the pH of the aqueous solution between before and after the γ-ray irradiation.

Examples 4 to 7 and Comparative Example 4

In each of Examples 4 to 7, the same procedures as in Example 1 were carried out except that the polypropylene glycol was replaced by the dihydric aliphatic alcohol as shown in Table 2, and the absorbed dose of the γ-rays was 25 kGg.

In Comparative Example 4, the same procedures as in Example 4 were carried out except that no propylene glycol was employed.

The test results are shown in Table 2.

TABLE 2

|  |  | Before γ-ray irradiation | | After γ-ray irradiation | |
|---|---|---|---|---|---|
| Example No. | Additive | Dextran 70,000 SC | Pressure resistance (kg/cm²) | Dextran 70,000 SC | Pressure resistance (kg/cm³) |
| Example 4 | Propylene glycol | 0.065 | 4.3 | 0.061 | 3.9 |
| Example 5 | Ethylene glycol | 0.068 | 4.1 | 0.070 | 3.8 |
| Example 6 | Diethylene glycol | 0.071 | 4.5 | 0.072 | 4.1 |
| Example 7 | Polyethylene glycol (MW: 1000) | 0.063 | 4.0 | 0.065 | 3.9 |
| Comparative Example 4 | None | 0.069 | 4.3 | 0.120 | 1.2 |

Table 2 shows that in Examples 4 to 7, between before and after the γ-ray irradiation, the change in the dextran 70,000 sieve coefficient of the hollow fibers was very small, the reduction in the pressure resistance of the hollow fibers was small, and the change in the ultraviolet-ray-absorption of the hollow fiber extract was less than 0.1, while in Comparative Example 4, the hollow fibers were significantly deteriorated or decomposed by the γ-ray irradiation.

Example 8 and Comparative Example 5

In each of Example 8 and Comparative Example 5, the same procedures as in Example 1 were carried out except that the aqueous solution contained 3% by weight of propylene glycol in Example 8 and 1% by weight of glycerol in Comparative Example 5. Before and after the γ-ray-irradiation, the weight and number average molecular weight (Mw and Mn) of the cellulose triacetate of the hollow fibers were measured.

The measurement results are shown in Table 3.

TABLE 3

|  |  | Example 8 3 wt % Propylene glycol aqueous solution | | Comparative Example 5 1 wt% Glycerol aqueous solution | |
|---|---|---|---|---|---|
|  |  | Mw | Mn | Mw | Mn |
| γ-ray irradiation | Before | $25.7 \times 10^4$ | $11.3 \times 10^4$ | $25.7 \times 10^4$ | $11.3 \times 10^4$ |
|  | After | $25.5 \times 10^4$ | $11.2 \times 10^4$ | $18.7 \times 10^4$ | $8.0 \times 10^4$ |

Table 3 clearly shows that in Example 8, the aqueous propylene solution satisfactorily prevents the reduction in molecular weight of the polymer due to the γ-ray irradiation, whereas in Comparative Example 5, the prevention effect of the aqueous glycerol solution to the reduction in the molecular weight of the hollow fiber polymer is poorer than that of aqueous propylene glycol solution. Namely, in Example 8, the retention of the molecular weight after the γ-ray irradiation is about 99.2%, and that in Comparative Example 5 was about 70%.

Referential Example 1 and Comparative Referential Examples 1 and 2

In Referential Example 1, an aqueous solution of 3% by weight of propylene glycol in a purified water by a reverse osmosis filtration was inoculated with a heat resistant bacteria, Batilus Pumilus, in the number as shown in Table 4. The inoculated aqueous solution was left at a temperature of 4° C. or 25° C. to culture the bacteria, and the number of the bacterial cells was counted 24 hours or 72 hours after the culture time.

In Comparative Referential Example 1, the same procedures as above were carried out except that the 3 weight % propylene glycol aqueous solution was replaced by distilled water.

Also, in Comparative Referential Example 2, the same procedures as above were carried out except that the 3 weight % propylene glycol aqueous solution was replaced by an aqueous solution of 1% by weight of glycerol.

The results are shown in Table 4.

TABLE 4

|  | Example No. | | |
|---|---|---|---|
|  | Referential Example 1 | Comparative Referential Example 1 | Comparative Referential Example 2 |
|  | Additive | | |
| Culture | 3 wt % Propylene glycol | Distilled water | 1 wt % Glycerol |
| time | Culture temperature | | |

| (hr) | 4° C. | 25° C. | 4° C. | 25° C. | 4° C. | 25° C. |
| --- | --- | --- | --- | --- | --- | --- |
| D | $3.4 \times 10^4$ | $3.4 \times 10^4$ | $2.6 \times 10^4$ | $2.6 \times 10^4$ | $1.6 \times 10^4$ | $1.6 \times 10^4$ |
| 24 | $3.2 \times 10^4$ | $3.8 \times 10^4$ | $2.6 \times 10^4$ | $2.0 \times 10^4$ | $4.3 \times 10^4$ | $3.5 \times 10^4$ |
| 72 | $2.9 \times 10^4$ | $3.1 \times 10^4$ | $3.0 \times 10^4$ | $2.8 \times 10^4$ | $8.2 \times 10^4$ | $6.9 \times 10^4$ |

Table 4 clearly shows that the 3% by weight propylene glycol aqueous solution substantially does not allow the proliferation of bacteria, the same as the distilled (sterilized) water. However, the 1% by weight glycerol aqueous solution allowed the proliferation of bacteria.

Example 9

The same procedures as in Example 8 were carried out by using the 3% by weight propylene glycol aqueous solution.

The γ-ray-sterilized blood dialyzer module was subjected to the same bacteria culture test as in Referential Example 1, except that no inoculation of the bacteria was carried out. After the 72 hour culture tests at 4° C. and 25° C., no bacterial cells were found in the blood dialyzer module.

Examples 10 and 11

In each of Examples 10 and 11 the, same procedures as in Example 1 were carried out with the following exceptions.

In Example 10, the aqueous solution was prepared by dissolving 10% by weight of a polyethylene glycol having an average molecular weight of 400 in water purified by the reverse osmosis filtration and saturated with molecular oxygen.

In Example 11, the aqueous solution was prepared by dissolving 10% by weight of propylene glycol in water purified by the reverse osmosis filtration and saturated with molecular oxygen.

The test results are shown in Table 5.

TABLE 5

| | | Item | | | |
| --- | --- | --- | --- | --- | --- |
| | | Before γ-ray irradiation | | After γ-ray irradiation | |
| Example No. | Additive | Dextran 70,000 SC | Pressure resistance (kg/cm$^2$) | Dextran 70,000 SC | Pressure resistance (kg/cm$^3$) |
| Example 10 | Polypropylene glycol (10 wt %) & oxygen | 0.072 | 3.4 | 0.072 | 2.9 |
| Example 11 | Propylene glycol (10 wt %) & oxygen | 0.069 | 3.4 | 0.068 | 3.3 |

Table 5 shows that the aqueous solution containing a dihydric aliphatic alcohol and saturated with oxygen effectively prevents the deterioration and decomposition of the polymeric dialyzing membranes.

Examples 12 and 13 and Comparative Example 6

In Example 12, a bundle of 48 core-in-sheath type composite fibers each consisting of a core portion consisting of a liquid paraffin and a sheath portion consisting of cellulose triacetate, was vertically suspended in a dryer at a temperature of 50° C. to allow the liquid paraffin to gravitationally fall down from the core portions of the composite fibers through the lower ends thereof and then centrifuged at a rotational speed of 3,000 rpm. About 95% by weight of the liquid paraffin in the core portions was removed.

The resultant bundle of hollow fibers were packed in a cylindrical case for a blood dialyzer module, the end portions of the hollow fiber bundle were sealed by applying a polyurethane resin to the end portions of spaces left between the hollow fiber peripheries and between the bundle and the inside surface of the cylindrical case and curing the resin at a temperature of 50° C. for 15 hours. A blood dialyzer module was obtained.

The hollow fibers in the blood dialyzer module were wetted with water by flowing one liter of water through the module, then a mixture of compressed air with water, namely a compressed air gas containing fine water particles dispersed therein, was flowed through the hollow spaces of the hollow fibers at flow rates of air of 100 liters/min and of water of 125 ml/min for 10 minutes to physically remove the residual liquid paraffin from the hollow fibers. Then, the dialyzer module was filled with water to prepare a wetted blood dialyzer module.

A pressure of 300 mmHg was applied alternately to the blood-feed side and to the blood-delivery side of the dialyzer module three times to withdraw the water. While the blood-delivery side of the dialyzer module was plugged, an aqueous humectant solution of 60% by weight of a polyethylene glycol having an average molecular weight of 400 was flowed into the blood dialyzer module through the blood-feed side thereof at a flow rate of 200 ml/min under a positive pressure for 5 minutes. Finally, air was blown under pressure from the blood-feed side and then from the blood-delivery side into the dialyzer module at a flow rate of 200 ml/min, each for one minute. The fine water particles introduced into the dialyzer module disappeared due to the humectant effect of the polyethylene glycol impregnated in the hollow fibers. Also the particles of the aqueous polyethylene glycol solutions remaining in the hollow spaces of the hollow fibers penetrated into the hollow fiber membranes and disappeared due to the application of pressure of two atmospheres at the blood-feed side to the dialyzer module.

The hollow fibers in the dialyzer module has an effective dialyzing area of about 1.5 m².

The blood dialyzer module having the hollow fiber bundle impregnated with the aqueous polyethylene glycol solution was subjected to an γ-ray irradiation at an absorbed dose of 25 kGy to sterilize the dialyzer module.

Before the γ-ray irradiation, the hollow fibers in the dialyzer module had a water content of 140 parts by weight per 100 parts by dry weight of the hollow fibers. The dialyzer module exhibited dialyzing performance and dextran 70,000 sieve coefficients, before and after the γ-ray irradiation as shown in Table 6.

In Example 13, the same procedures as in Example 12 were carried out except that the polyethylene glycol was replaced by propylene glycol. The test results are shown in Table 6.

(3) Dextran 10,000 dialyzability (Dextran 10,000 DA)

This was determined in the same manner as the determination of the urea dialyzability except that an aqueous solution of 0.02% by weight of dextran having a molecular weight of 10,000 was dialyzed, in place of the 0.01% urea aqueous solution.

Table 6 also shows the dialyzing performance and dextran 70,000 SC of the dialyzing modules of Examples 10 and 11, after leaving the γ-ray-sterilized dialyzing modules at a temperature of 80° C. for 300 hours or at a temperature of −5° C. for 100 hours, in Table 6.

TABLE 6

| Example No. | Aqueous solution | Treatment | Dialyzing performance | | | Dextran 70,000 SC |
|---|---|---|---|---|---|---|
| | | | Dextran 10,000 DA (ml/min) | Urea DA (ml/min) | UFR (ml/m²/hr/mmHr) | |
| Example 12 | 60 wt % polyethylene glycol aqueous solution | Before γ-ray sterilization | 48 | 190 | 230 | 0.07 |
| | | After γ-ray sterilization | 47 | 192 | 231 | 0.07 |
| | | 80° C., 300 hrs | 49 | 194 | 232 | 0.07 |
| | | −5° C., 100 hrs | 45 | 193 | 233 | 0.07 |
| Example 13 | 60 wt % propylene glycol aqueous solution | Before γ-ray sterilization | 49 | 197 | 223 | 0.06 |
| | | After γ-ray sterilization | 48 | 196 | 233 | 0.06 |
| | | 80° C., 300 hrs | 47 | 198 | 228 | 0.06 |
| | | −5° C., 100 hrs | 47 | 195 | 235 | 0.06 |
| Comparative Example 6 | Pure water | Before γ-ray sterilization | 47 | 193 | 223 | 0.06 |
| | | After γ-ray sterilization | 47 | 193 | 250 | 0.08 |
| | | 80° C., 300 hrs | 43 | 190 | 270 | 0.12 |
| | | −5° C., 100 hrs | Froze and leaked | | | |

In Comparative Example 6, the same procedures as in Example 12 were carried out except that no polyethylene glycol was employed. The test results are shown in Table 6.

The dialyzing performance was measured by the following test methods.

(1) Water-permeability (UFR)

Purified water in amount of 20 ml was permeated through the dialyzing module under a differential pressure of 300 mmH₂O (2,942 Pa) between the blood-feed and -delivery sides at a temperature of 35° C. A time necessary for completing the permeation of 20 ml of the purified water was measured. From the measured permeating time, the amount of water, the effective dialyzing area and the differential pressure, the water permeability of the hollow fibers were calculated in units of ml/m²/hr/mmHg.

(2) Urea dialyzability (Urea DA)

An aqueous solution of 0.01% by weight of urea was flowed through the hollow spaces of the hollow fibers in the module, at a temperature of 37° C. at a flow rate of 200 ml/min, while allowing a portion of urea in the aqueous solution to be dialyzed through the hollow fibers, and the difference in concentration of urea between the supplied urea solution into an end of the module and the delivered urea solution from the opposite end of the module was measured.

The urea dialyzability of the hollow fiber bundle was calculated from the concentration difference.

We claim:

1. A method of sterilizing a blood dialyzer having semipermeable polymeric dialyzing membranes by γ-ray irradiation, comprising the steps of:

impregnating semipermeable polymeric dialyzing membranes in a blood dialyzer with an aqueous solution of at least one dihydric aliphatic alcohol which is γ-ray-absorbable and water soluble and is present in an amount of 3 to 300% based on the total weight of the semipermeable polymeric dialyzing membranes in the aqueous solution; and γ-ray irradiating the semipermeable polymeric dialyzing membranes impregnated with the aqueous solution of the dihydric aliphatic alcohol in the wetted condition.

2. The sterilizing method as claimed in claim 1, wherein the dihydric aliphatic alcohol is selected from the group consisting of the compounds of the formulae (I) and (II):

(I)

and

-continued

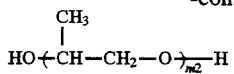
(II)

wherein n represents an integer of 2 to 5, $m_1$ represents an integer of 1 to 50, and $m_2$ represents an integer of 1 to 10.

3. The sterilizing method as claimed in claim 1, wherein the dihydric aliphatic alcohol is selected from the group consisting of ethylene glycol, propylene glycol, polypropylene glycol, polyethylene glycol and ethylene glycol-propylene glycol copolymers.

4. The sterilizing method as claimed in claim 1, wherein the dihydric aliphatic alcohol has a molecular weight of 1,500 or less.

5. The sterilizing method as claimed in claim 1, wherein the dihydric aliphatic alcohol is present in a concentration of 0.1 to 80% by weight in the aqueous solution.

6. The sterilizing method as claimed in claim 1, wherein during the entire period of and after the γ-ray irradiation, the pH of the aqueous solution of the dihydric aliphatic alcohol is maintained at a level of 4 to 7.

7. The sterilizing method as claimed in claim 1, wherein a pH-adjuster is added to the aqueous solution of the dihydric aliphatic alcohol to control the pH of the aqueous solution of the dihydric aliphatic alcohol to a level of 4 to 7 during the entire period of and after the γ-ray irradiation.

8. The sterilizing method as claimed in claim 7, wherein the pH-adjuster is selected from the group consisting of phosphate buffer solutions and borate buffer solutions.

9. The sterilizing method as claimed in any one of claims 6, 7 and 8, wherein a difference in pH of the aqueous solution of the dihydric aliphatic alcohol between before and after the γ-ray irradiation is in the range of less than 1.5.

10. The sterilizing method as claimed in claim 1, wherein the γ-ray irradiation is carried out at an absorbed dose of 20 to 50 kGy.

11. The sterilizing method as claimed in claim 1, wherein the semipermeable dialyzing membranes are in the form of hollow fibers.

12. The sterilizing method as claimed in claim 1, wherein the semipermeable dialyzing membranes comprises at least one polymeric material selected from the group consisting of cellulose, cellulose diacetate, cellulose triacetate, alkyl methacrylate homopolymer and copolymers, polyvinyl alcohol, partially saponified polyvinyl acetates, polysulfone, acrylonitrile-homopolymer and copolymers, polyethylene, and polyamides.

13. The sterilizing method as claimed in claim 1, wherein the aqueous solution of the dihydric aliphatic alcohol is saturated with oxygen dissolved therein.

14. The sterilizing method as claimed in claim 1, wherein the aqueous solution impregnated in the semipermeable polymeric dialyzing membranes has a concentration of the dihydric aliphatic alcohol of 500 to 1000 g/l.

15. The sterilizing method as claimed in claim 1, wherein in the impregnating step, the blood dialyzer is packed with the aqueous solution of the dihydric aliphatic alcohol in a concentration of 5 to 50 g/l.

16. The sterilizing method as claimed in claim 1, wherein during the γ-ray irradiation step, the temperature of the semipermeable polymeric dialyzing membranes is maintained at a level of 50° C. or less.

17. The sterilizing method as claimed in claim 1, wherein before the impregnating step, the semipermeable polymeric dialyzing membranes are present in a semi-wetted condition.

* * * * *